(12) United States Patent
Schaeffer et al.

(10) Patent No.: US 7,120,353 B2
(45) Date of Patent: Oct. 10, 2006

(54) INFRARED SAUNA

(76) Inventors: Bernarr C. Schaeffer, 725 Rte. 213, Rosendale, NY (US) 12472; James Schaeffer, 725 Rte. 213, Rosendale, NY (US) 12472; Wayne Schaeffer, 101 Vincent La., Stone Ridge, NY (US) 12484

( * ) Notice: Subject to any disclaimer, the term of this patent is extended or adjusted under 35 U.S.C. 154(b) by 492 days.

(21) Appl. No.: 10/079,397

(22) Filed: Feb. 20, 2002

(65) Prior Publication Data

US 2003/0156831 A1    Aug. 21, 2003

(51) Int. Cl.
*A21B 2/00* (2006.01)
(52) U.S. Cl. ............ 392/416; 392/435; 392/436; 392/437; 219/530; 219/531; 219/539; 219/540
(58) Field of Classification Search ........... 392/416, 392/435, 436, 437; 4/524; 219/530, 540, 219/528, 548, 212, 539, 531
See application file for complete search history.

(56) References Cited

U.S. PATENT DOCUMENTS

| | | | | |
|---|---|---|---|---|
| 3,342,977 A * | 9/1967 | Anderson | .................... | 219/548 |
| 4,485,297 A * | 11/1984 | Grise et al. | ................. | 219/528 |
| 4,900,900 A * | 2/1990 | Shirae et al. | ............... | 219/501 |
| 4,908,497 A * | 3/1990 | Hjortsberg | .................. | 219/539 |
| 4,998,006 A * | 3/1991 | Perlman | ..................... | 219/212 |
| 5,036,177 A * | 7/1991 | Pagliarini, Jr. | .............. | 219/212 |
| 5,059,756 A * | 10/1991 | Henschenp et al. | ...... | 219/85.22 |
| 5,081,341 A * | 1/1992 | Rowe | ......................... | 219/505 |
| 5,117,481 A * | 5/1992 | Sung | ......................... | 392/416 |
| 5,206,485 A * | 4/1993 | Srubas et al. | ............... | 219/549 |
| 5,224,927 A * | 7/1993 | Tapper | ....................... | 604/20 |
| 5,410,127 A * | 4/1995 | LaRue et al. | ............... | 219/212 |
| 5,504,309 A * | 4/1996 | Geissler | ..................... | 219/663 |
| 5,649,972 A * | 7/1997 | Hochstein | .................... | 607/100 |
| 5,751,896 A * | 5/1998 | Sandhu | ....................... | 392/416 |
| 5,889,923 A * | 3/1999 | Lee et al. | .................... | 392/435 |
| 5,912,811 A * | 6/1999 | Mackta | ....................... | 363/45 |
| 6,043,471 A * | 3/2000 | Wiseman et al. | ........... | 219/662 |
| 6,142,927 A * | 11/2000 | Clark | ............................ | 600/9 |
| 6,166,357 A * | 12/2000 | Kim | ............................. | 219/529 |
| 6,272,697 B1 * | 8/2001 | Park | ............................. | 4/524 |
| 6,294,769 B1 * | 9/2001 | McCarter | .................... | 219/544 |
| 2002/0046422 A1* | 4/2002 | Perett | ............................ | 4/524 |

FOREIGN PATENT DOCUMENTS

| | | | |
|---|---|---|---|
| JP | 403097462 | * | 4/1991 |
| JP | 404279166 | * | 10/1992 |
| JP | 406063093 | * | 3/1994 |
| JP | 410170000 | * | 6/1998 |

(Continued)

*Primary Examiner*—Robin O. Evans
*Assistant Examiner*—Leonid M. Fastovsky
(74) *Attorney, Agent, or Firm*—Joseph B. Taphorn (57) ABSTRACT

A portable compact sauna wherein a user's body is warmed to sweating primarily by direct absorption of infrared radiation. Broad infrared radiation emitters or sources are placed around the inside of a narrow cabinet so as to be in close proximity to various parts of a seated user. Fins spaced apart less than finger-width on the emitters protect the user from contact with elevated temperatures in the emitters. The emitters, which lend themselves to easy cleaning, are heated by electric infrared heaters having a unique design which eliminates extremely-low-frequency (ELF) electromagnetic field (ELF) normally generated by AC energized electrical heater elements, to provide low extremely-low frequency EMF saunas able to utilize conventional-commercial electrical-energy sources. The emitters protect the heaters. Power wires for the heaters are arranged for low ELF EMF emission, too.

1 Claim, 11 Drawing Sheets

FOREIGN PATENT DOCUMENTS

| | | | |
|---|---|---|---|
| JP | 2002011069 | * | 1/2002 |
| JP | 2003051368 | * | 2/2003 |

* cited by examiner

INFRARED SAUNA

INTRODUCTION

1. Field of the Invention

This invention relates to saunas, and more particularly to a portable sauna employing infrared heat.

2. Background of the Invention

The use of saunas to promote the formation of perspiration (sweating) for its therapeutic effects, is well known. However, the use of saunas relying primarily on the body deep absorption of infrared radiation, is not known. While the provision of a sauna cabinet per individual is known, such individual cabinets have not been compact or portable.

The use of infrared heaters throughout history is well known. Humans first warmed themselves with campfires, later with fireplaces, and now with radiant floors and infrared sauna rooms. However, heretofore when using any infrared source greatly warmer than room temperature, it was difficult to protect a user from touching the hot surface (and experiencing pain or burning) without disadvantageously shielding the heat source in the process. Therefore the emitting surface was either placed far away from the user or had a bulky screen placed around it. In either case, the heater could not safely be in close proximity to the user.

3. Prior Art

Books discussing saunas include "Sweat" authored by Michael Aaland and published by Capra Press, Santa Barbara, Calif. (1978); "Therapeutic Heat and Cold", $2^{nd}$ Edition, Vol.2 of the "Physical Medicine Library" published by Elizabeth Licht, New Haven, Conn. (1972) (page 203 article "History of Therapeutic Heat" by Sidney Licht with Herman L. Kamenetz); "Light Therapeutics: A Practical Manual of Phototherapy for the Student and the Practitioner", Revised Edition, authored by Dr. John Harvey Kellogg and published by The Good Health Publishing Co., Battle Creek, Mich. (1910); and "The Sauna is . . . " authored by Bernhard Hillila and published by Penfield Press, 215 Brown St., Iowa City, Iowa 52245 (1988).

Sidney Licht, in his article above identified, notes that in 1891, Dr. Kellogg built a rectangular cabinet with 40 lamps of 20 candle power each, and interior reflectors, in which his patients sat completely nude, with the head outside. But Kellogg's cabinets were roomy, to assure that the patient did not come in contact with the hot lamps radiation source. Thus his patient was not directly heated primarily by radiation, but rather by a combination of radiation and convection; heating by radiation being defined as the direct absorption by the body of the patient of the infra red energy emanated by the heater (lamps in Dr. Kellogg's case); and heating by convection being defined as direct contact with the body of the patient by a moving substance (air) warmed as by the lamps.

Other infrared saunas are known. Typically, they are room-sized, having several heater panels imbedded in the walls far from the user or mounted behind bulky metal screen shields: in either case the heater could not safely be in proximity to the user; proximity being advantages for efficiency of heat transfer and for compactness of a heating apparatus. Such saunas donot impact the body deeply, or evenly over a large expanse of its surface area, because of the comparatively small area of the room that is covered by heaters, and because while some may be very close others are very far from the user. Moreover, a room-sized sauna is not easily portable and will not efficiently or evenly heat a human user.

Non-lamp infrared heaters are known.

Actually, infrared heaters are ubiquitous in industrial processing application, where various safety protocols and structures protect workers from injury in their usage. Infrared heaters for personal heating are well known in radiant floor and ceiling applications, and in baby incubators, for example, where the temperature of the heating surface is low enough, or the heater is far enough from the user, as to not be a danger.

Researchers have opined that fields of electromagnetic radiation (EMFs) in the extremely low frequency (ELF) band, e.g. 60 Hz, may be harmful to the human body if they are stronger than ambient fields levels (typically, near or less than one milligauss). See, for example, the book "Cross Currents" written by William O. Becker and published by Penguin Putnam Inc. in 1990, and the book "Currents of Death" written by Paul Brodeur and published by Simon and Schuster in 1989.

Existing infrared saunas can have upwards of 25 to 50 milligauss ELF EMF impacting the body. Very expensive high-nickel content metal shields exist that absorb EMF, but have yet to be employed over high surface area infrared heaters—they are cost prohibitive.

U.S. Pat. No. 5,399,996 Yates et al shows a technique for minimizing electromagnetic emissions. It uses a dummy load circuit which has an impedance equal to that of the circuit load, in a digital environment.

SUMMARY OF THE INVENTION

Accordingly, it is an object of the invention to provide a compact sauna usable not only in the home but also in health clubs, hotels, detoxification clinics, etc.

An additional object of the invention to provide a portable sauna, and one that will pass through the normal 36-inch-wide door of a conventional home.

Another object of the invention is to provide a sauna which primarily heats the user directly by infrared radiation.

Another object of the mention is to provide a sauna which utilizes broad infrared heat sources or emitters in close proximity to the user's various body parts.

Still another object of the invention is to provide a sauna which allows the infrared heat source or emitter to be safely placed close to the user's body.

Still another object of the invention is to provide a sauna using an electric infrared heater to heat the infrared heat source or emitter in close proximity to the user's body.

An additional object of the invention is to provide a sauna that is easy to clean and durable in use.

Yet another object of the invention is provide a sauna using conventional 110-volt 60-cycle current electric infrared heaters and yet has a low extremely-low-frequency (ELF) electromagnetic field (EMF) in it.

A further object of the invention is to provide an infrared emitter and infrared heater assembly that is safe to touch while hot enough to transfer significant heat to the user.

A still further object of the invention is to provide an infrared emitter and infrared heater assembly that is of programmable size, shape, color, physical strength, warm-up time, temperature, and heat-source type.

A yet further object of this invention is minimize cabinet ELF EMF dale to AC power wiring for the heaters.

Another object of the invention is to provide an infrared emitter and infrared heater assembly that is safe and effective for such applications as very-close-range personal heaters for use in offices (e.g., under desks), at home, in factory and commercial environments, in hospitals and baby incubators, and the like.

A further object of the invention is to provide a portable sauna that is inexpensive of construction and easy of manufacture.

The objects of the invention are accomplished through the provision of a small sauna having safe-to-the-touch infrared emitters or sources of a large surface area surrounding the user's body on all sides. The infrared radiation sources or emitters are of a unique design. The infrared radiation source or emitter incorporates protrusions such as parallel fins spaced close enough to thwart fingers being inserted between them, and extending outward from a hot base portion (flats between the fins and main radiators) heated to elevated temperatures but which at their outer or free ends are at comfortable-to-touch temperature due to the low heat conductance of the material of which the source is constructed and to the heat loss along the depth of the fins due to radiation and air cooling. The cool-to-the-touch radiation source enables construction of a small cabinet conforming to the configuration of a person seated in it, with a plurality of infrared heat sources or emitters being located in close proximity to and around the person's body parts.

The finned infrared radiation sources are easy to clean and protect their heaters behind them. A light wiping action of the finned sources is just about all that is needed to keep the sauna tidy and operational.

The infrared radiation sources or emitters are heated by electric infrared heaters positioned behind them in close proximity. The use of electric infrared heaters powered by conventional 110 volt 60 cycle alternating current and positioned in close proximity to the infrared radiation sources and hence to the users, is enabled by the design of unique electric infrared heaters generating only low extremely-low-frequency (ELF) electromagnetic fields (EMFs) in the sauna by canceling them out. The unique dual electric infrared heaters may be formed of a plastic substrate on both sides of which are printed semi-conductor patterns having a) a plurality of identical electrically-resistive bars spaced apart from each other and radiating infrared energy when electrical current is passed through them, and b) a pair of longitudinal stripes extending parallel to and spaced from each other and interconnected with respective ends of the bars to have electrical connections therewith to form two thin flat planar electrical resistance heaters in very close proximity to each other; and electrically connecting them to the AC source so that the heaters are respectively wired to opposite electrical polarities. Thus a set plurality of identical bars that are spaced apart from each other and radiate infrared energy when electrical current is passed through them, are mounted next to an identical set of such bars wherein electricity is simultaneously passed through in the opposite direction; the EMFs generated by corresponding bars of each set canceling each other. Of course, two single heater arrays (on separate substrates) may be juxtaposed, with opposite current flow, to achieve reduced EMF effects, too.

Electric infrared heaters may so be powered by direct current, the electrical connections needing to be reversed for the respective heaters only if all electro-magnetic fields are to be minimized.

Another way to heat the emitters is by circulation of a heat exchange fluid behind them, as through channels integral with the valleys or bases of the finned emitter. This would eliminate the AC EMF problem too, but entails a cumbersome structure.

A feature of the invention is that it enables taking full advantage of the special heating powers of infrared radiation by relying primarily on it. Whereas steam or warm air heats only the skin of a sauna user (by conduction), strong infrared radiation soothingly penetrates the body to about one and one-half inches to more effectively and comfortably warm the body to sweating temperature and more effectively remove body toxins which primarily reside in the fatty tissues immediately under the skin. Strong infrared radiation penetrates more deeply into the body than does heat from hot air or steam, and thus causes the body to sweat at lower temperatures, accommodating users who dislike higher temperatures. Deep penetration causes weight loss in fat, not just in water.

An advantage of the invention is that the close location or proximity of the infrared sources or emitters to the user's body, and the close location or proximity of the electric infrared heaters to the infrared sources, allows the walls of the sauna cabinet to be closely positioned about the users body, resulting in a compact cabinet which not only frugally and effectively uses heat (requiring less electricity, and applying it more precisely, deeply, and intimately), but can be dimensioned to pass through normal-width entrance doors to homes and business establishments.

Low ELF EMF is insured within the cabinet also by constructing the heater power lines in extremely-low-frequency electro-magnetic-field canceling arrangements.

BRIEF DESCRIPTION OF THE DRAWINGS OF PREFERRED EMBODIMENTS

These and other objects, features and advantages of the invention will become apparent from a reading of the following detailed description of a preferred embodiment of the invention, when considered with the appended drawings wherein.

DETAILED DESCRIPTION OF PREFERRED EMBODIMENTS

Figure 1:
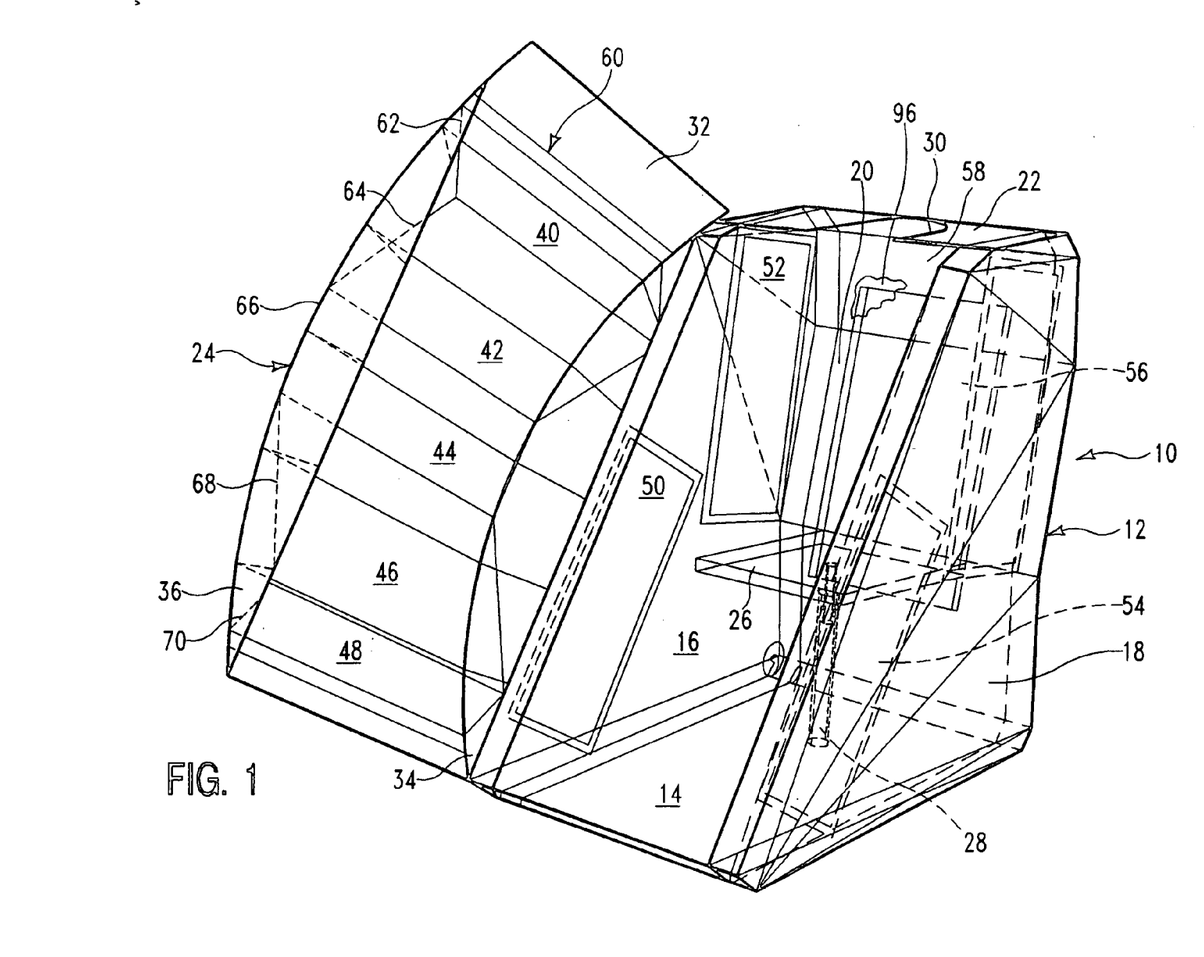
FIG. 1 is a diagrammatic view in perspective of a portable sauna constructed according to the invention.

Referring now particularly to the drawings, there is shown in FIG. 1 a portable compact sauna generally indicated by the numeral 10. The sauna 10 includes a narrow cabinet generally indicated by the numeral 12 and including a floor 14, a right-hand side wall 16, a left-hand side wall 18, a rear wall 20, a roof 22, and an upwardly rearwardly-sloping front opening closed by a side-hinged door generally indicated by the numeral 24. The rear wall 20 may hingedly mount at adjustable chair heights a forwardly extending seat 26 supported at its forward end upon a height-adjustable floor post 28. The roof is cutout at 30 receive the neck of a user seated on seat 26 adjusted to an appropriate height, leaving the user's head outside of the sauna cabinet 12.

The door 24 includes a rearwardly upwardly-curving cylindrical-like arc or front portion 32 and a fight-hand siding 34 and left-hand siding 36 bridging the arc of the front portion 32. The door 24 is hinged to the cabinet right-hand side wall 16 along the free edge of its right-hand door siding 34 as by a conventional piano hinge. The cabinet components may be made of a suitable plastic such as polyester ABS or PETG. It will be appreciated that the rearwardly upwardly-sloping front edges of the of the cabinet side walls 16 and 18 enables the cabinet when the door 24 is in closed position, to snugly accommodate in its bottom portion the horizontally-extended legs of a seated user while in its upper portion closely embracing the user's torso (see FIG. 6).

A number of infrared sources or emitters are distributed about the interior surface of the cabinet. In the preferred embodiments disclosed, ten flat and broad sources are employed: five being mounted on the door 24; five being mounted on the cabinet walls. Door infrared sources from top to bottom are numbered 40, 42, 44, 46 and 48. Cabinet right-side wall sources are numbered 50 and 52, cabinet left-side wall sources are numbered 54 and 56, and rear-wall source is numbered 58.

Figure 5:
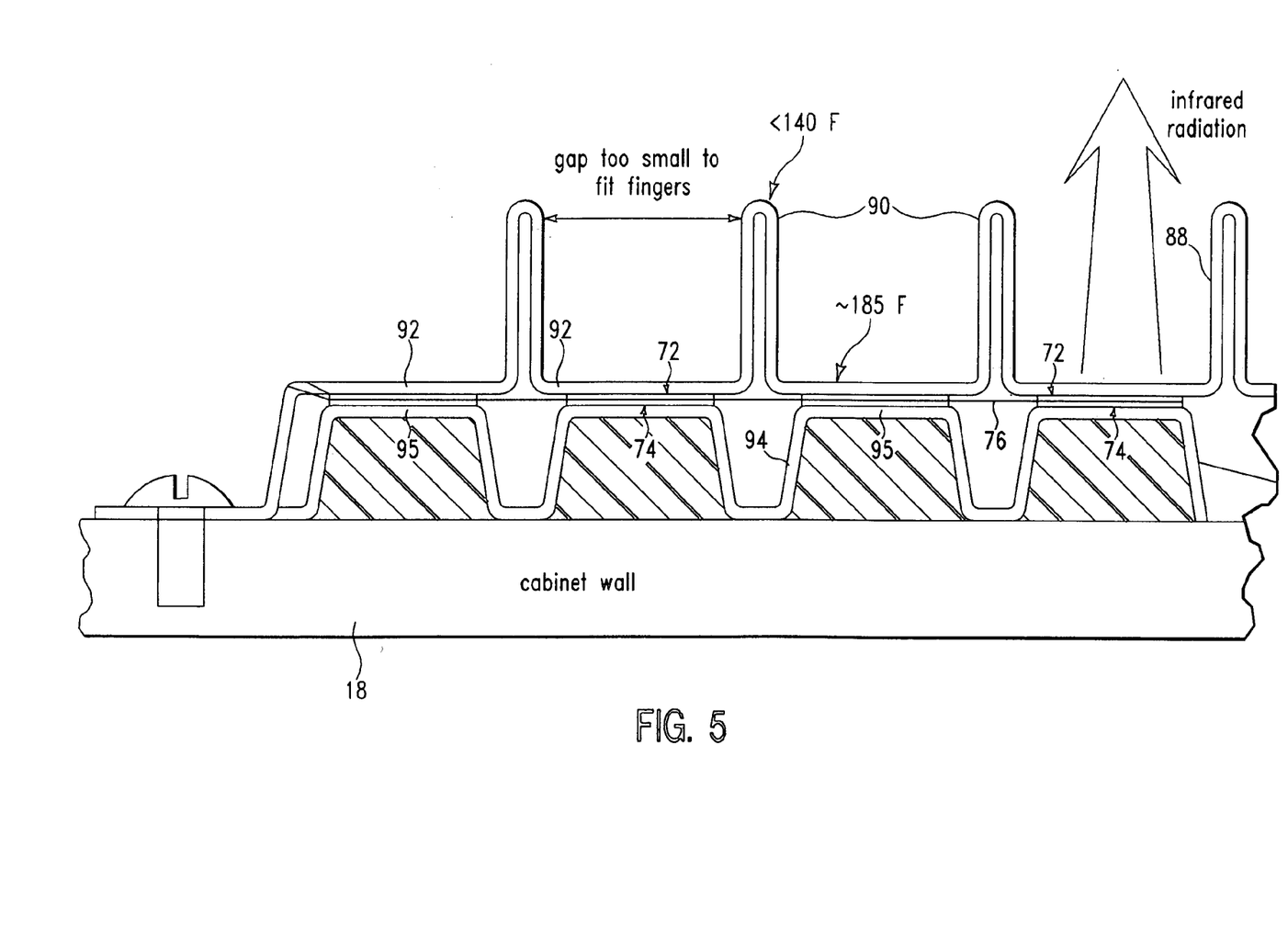
FIG. 5 is a cross-sectional view showing a dual electric infrared heater according to the invention (1) mounted in spaced relationship via a backing panel on a cabinet wall to avoid undesirable heating of the wall, and (2) covered by the unique infrared source or emitter it heats and that presents the person with only a warm-surface tactile exposure.

The door sources 40–48 are mounted indirectly on the door via an upper-and-lower-end attached panel generally indicated by the numeral 60 and following the inclination of the door 24 and bent at four different places to present five different sections or faces 62, 64, 66, 68, 70 for mounting flat, directional infrared sources at various angles to the sauna user's body parts. In general panel 60 follows the contours of the front of a person sitting in the sauna on seat 26. The top and bottom sections 62 and 70 of the panel are generally coplanar, and dispose flat panel sources 40 and 48 thereon to radiate infrared energy rearwardly and slightly downwardly into the sauna cabinet (FIGS. 1 and 5). Adjacent sections 64 and 68 are respectively inclined downwardly and rearwardly and respectively dispose flat panel sources 42 and 46 thereon to radiate infrared energy downwardly and rearwardly into the sauna cabinet. The central panel section 66, interconnecting sections 64 and 68 and generally in a parallel plane with top and bottom sections 62 and 70, mounts source 44 to radiate infrared energy somewhat downwardly and rearwardly in the sauna cabinet. Source 40 radiates the front of the upper portion of the torso of a user seated on seat 26; source 42 his or her thighs; source 44 the knee areas; source 46 the upper lower legs; and source 48 the lower legs and feet.

Cabinet right-side wall 16 sources 50 and 52 radiate the right side of a user. Lower cabinet source 50 warms the outside of the right leg; source 52 the right-side of the torso.

Cabinet left-side wall 18 sources 54 and 56 radiate the left side of a user. Lower cabinet source 54 warms the outside of the left leg; source 56 the left side of the torso.

Cabinet rear wall source 58 radiates the back of a user.

The infrared source or emitter employed in the invention and generally indicated by the numeral 88 (FIGS. 4 and 5), is comfortable to the human touch on its exposed side. The source may be vacuum formed of a sheet of suitable plastic such as polycarbonate, and with hollow fins 90 that are spaced less than one-half inch apart (less than normal finger width and that project about one-half inch high from a base 92. When a electric infrared heater is placed behind the finned infrared source or emitter, the flats constituting the base 92 between the fins are heated to a high infrared radiating temperature, as on the order of 200 degrees Fahrenheit or more. The chosen plastic or other material for the fins has poor heat conductance; between the cooling of the fins by radiation and air movement over their surfaces, the fin tip temperature is limited to 140 degrees F. or so even though the temperatures of the flats in the base 92 reach 200 degrees F. or so. The small spacing of the fins, less than finger width, limits the exposure of the user to the tip temperature of 140 degrees. Hence higher infrared source or emitter temperatures than heretofore practical can be utilized. The finned infrared source may be also be deemed a cover, and so molded, for an electric infrared heater used to heat the sauna infrared source or emitter 66 base 92 to efficient infrared radiating temperature.

Figure 4:
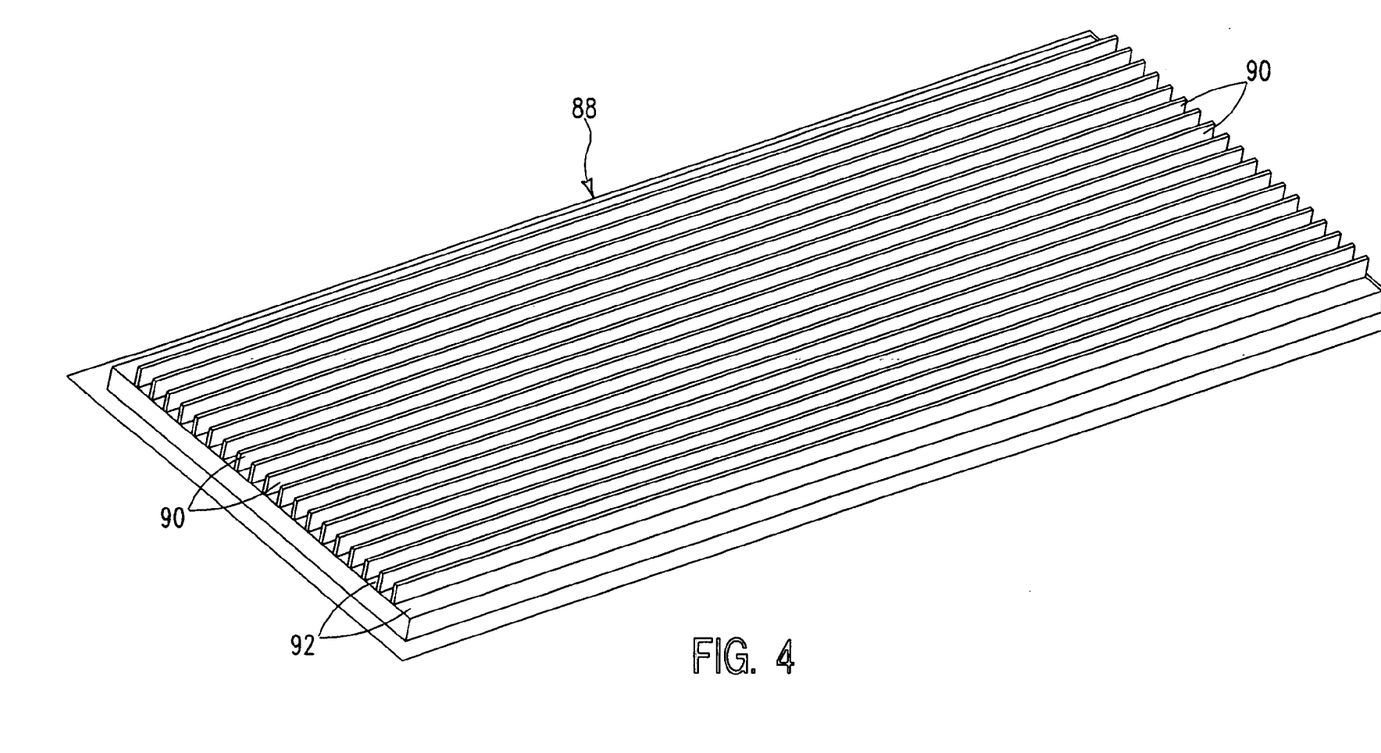
FIG. 4 is an isometric view in perspective of the infrared source or emitter for the sauna finned to block a person's body parts from contacting the portions thereof at elevated temperatures.

As observed earlier, the hollow finned infrared source or emitter (and cover) 88 of FIGS. 4 and 5 may be vacuum formed from a suitable sheet of plastic. Alternatively, a solid-, and thinner-, finned infrared source or emitter may be injection molded.

The electric infrared heaters for heating the infrared sources 88 may be generally of the type described in U.S. Pat. No. 4,485,297. Such a heater is formed of a plastic substrate on which was printed as by silk screening a semi-conductor pattern having a) a plurality of identical electrically-resistive bars spaced apart from each other and radiating infrared energy when electrical current is passed through them, and b) a pair of longitudinal stripes extending parallel to and spaced from each other and interconnected with respective ends of the bars to form electrical connections therewith; a metallic conductor like copper overlying each longitudinal stripe and in intimate electrical contact therewith throughout its length; a pair of plastic sheets positioned on respective sides of the substrate and pattern and hermetically sealing them; and a pair of crimp-on connectors for establishing electrical connection with the conductors.

But it has been found that electric infrared heaters constructed according to the U.S. Pat. No. 4,485,297 emanate a high extremely-low-frequency (ELF) electromagnetic field (EMF), such as 25 mg at very close range. Thus a unique heater assembly which only produces a low extremely-low-frequency EMF has been invented and utilized in the sauna. The unique heater assembly mounts two thin flat planar electrical resistance heaters of the type disclosed in U.S. Pat. No. 4,485,297 in very close proximity to each other and wires them respectively to opposite AC electrical polarity. Thus the set plurality of identical bars that are spaced apart from each other and radiate infrared energy when electrical current is passed through them, are juxtaposed to an identical set of such bars so that when electricity is simultaneously passed through them in opposite directions, the ELF EMFs generated by corresponding bars of each set cancel each other near totality.

Figure 2:
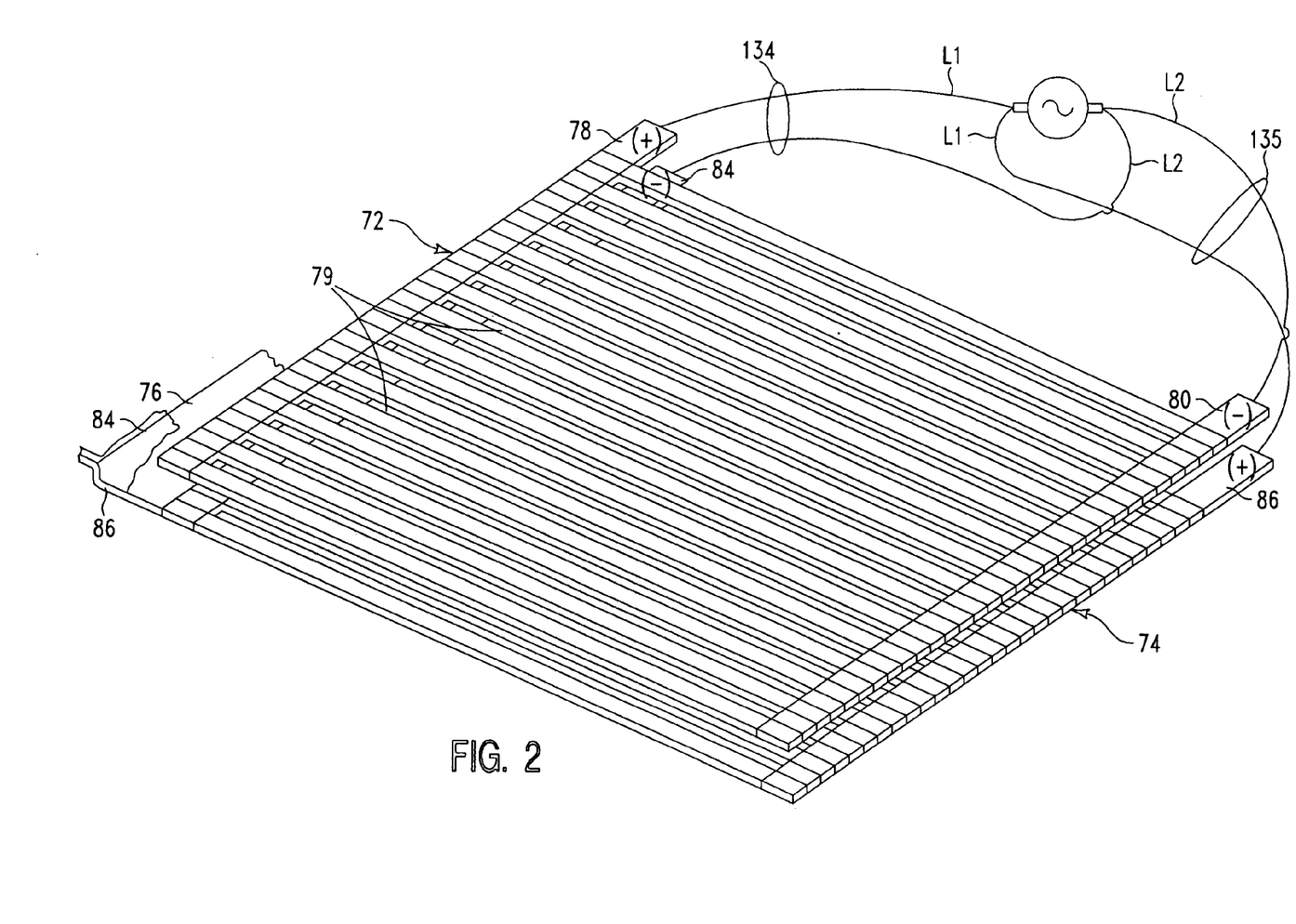
FIG. 2 is an partial isometric view in perspective of the two infrared generating components of a dual infared heater used in the sauna and showing their reversed electrical connections with an AC source to minimize ELF EMF generation.

In a preferred embodiment and as shown in FIG. 2, two thin flat planar electrical resistance heaters generally indicated by the numeral 72 and 74 are mounted on opposite sides of a single plastic substrate 76 of polycarbonate or the like. The conductor stripes 78 and 80, interconnecting electrically-resistive radiating bars 79 of heater 72, are connected one way to a source 82 of alternating current (AC), while corresponding conductor stripes 84 and 86 are connected the opposite way to the AC source 82. Thus at any given time, current flows in opposite ways through corresponding ones of the bars of the two heaters, effectively neutralizing the EMF generated by each. This enables the dual infrared heaters to be placed close to the human body without danger of impacting the body of the user with high doses of extremely-low-frequency electromagnetic fields (ELF EMFs).

Figure 3:
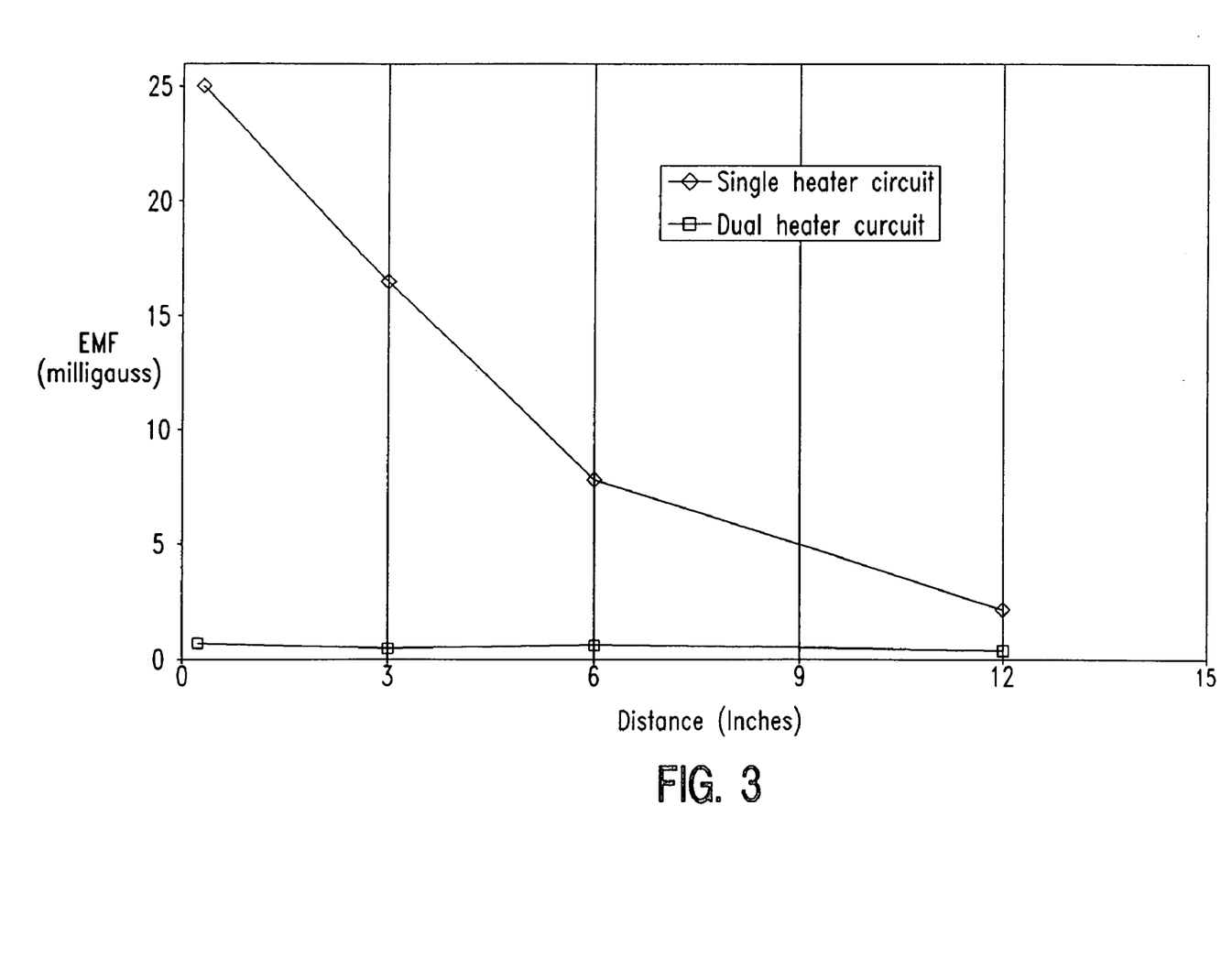
FIG. 3 is a chart depicting empirical evidence showing the high ELF EMF resulting from using single electric infrared heaters, versus the low ELF EMF resulting from using dual electric infrared heaters with reversed electrical connections.

As shown in the chart of FIG. 3, a significant reduction of measured EMF strength obtains from the use of a dual heater assembly over a single heater assembly. For a single circuit heater, a high extremely-low-frequency EMF of 25 milligauss may obtain within one inch of it, and of about 16 milligauss at 3 inches. For the dual circuit heater of the invention, approximately only 1 milligauss obtains at even only 1 inch distance.

It will be appreciated that the electrically-resistive radiating bars 79 of heater 72 may be replaced with suitably-mounted high-resistance wiring such as nichrome, in solid, mesh or fabric construction.

It will also be appreciated, as observed earlier, that the heaters may be powered with direct current, in which case the extremely-low-frequency EMF does not obtain.

As per the showings of the U.S. Pat. No. 4,485,297, the dual heater of FIG. 2 above could be hermetically sealed between two sheets 84 and 86 of plastic (here polycarbonate) and crimp-on connectors employed to make electrical connections.

Figure 7:
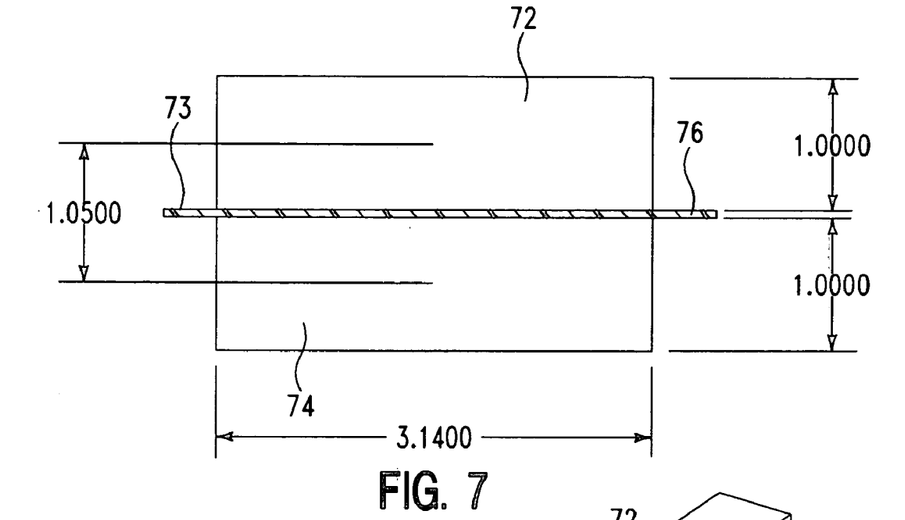
FIG. 7 is an edge sectional view of a portion of a flat panel electric infrared heater showing a pair of flat resistance-heating bars on opposite sides of an insulating substrate and through which respective side bars 60 cycle alternating current instantaneously flows in opposite directions to produce canceling ELF EMFs.

Of course, single heater arrays on separate substrates may be juxtaposed, with corresponding electrically-resistive bars opposed and wired to opposite polarity, to achieve similar reduced EMF effects. However, best extremely-low-frequency EMF reduction is achieved by positioning the thin flat wiring or bars 72 and 74 on opposite sides of a thin substrate 76, in a manner shown in FIG. 7.

Figures 7A, 8, 8A:
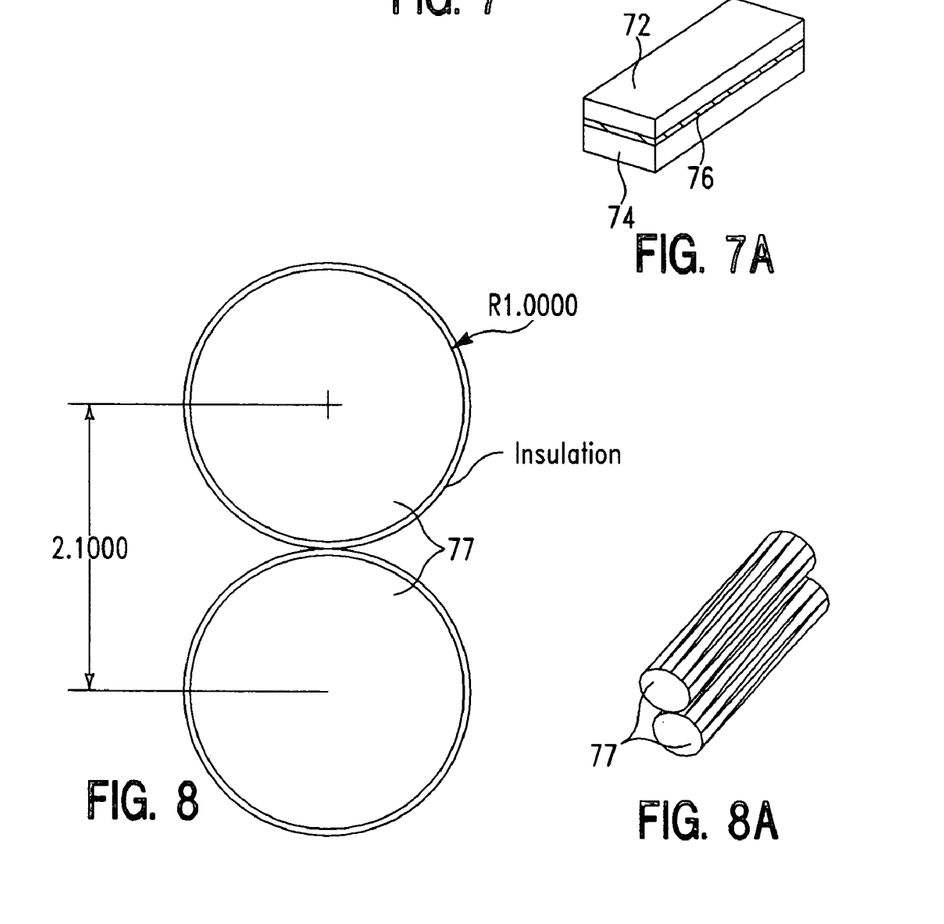
FIG. 7A is a view in perspective of the two heating bars of FIG. 7.
FIG. 8 is a sectional view of two round insulation-clad electrical wires, to show the inherently greater spacing of electrical currents in juxtaposed round wires over that of juxtaposed flat wires and hence their greater inability to cancel EMFs as effectively as flat wires of FIG. 7 and 7A.
FIG. 8A is a view in perspective of the two round wires of FIG. 8.

FIG. 8 shows graphically why insulated round wires cannot be as closely positioned, low extremely-low-frequency EMF-wise, as insulated flat wires; the center of conductivity for abutting insulated round wires 77 being inherently necessarily further apart than for abutting flat wires; hence round wires are less able to effect low ELF EMFs than flat wires.

A specific infrared source or emitter and an electric infrared heater therefor and mounting structure assemblage, are shown in FIG. 5. A cabinet wall, such as left-side wall 18 backs up a corrugated panel 94 in which ridges 95 are arranged in correspondence with the electric infrared heaters 72 and 74 corresponding pairs of bars 79, and the infrared source's valleys or bases 92, to hold them snugly together. The finned infrared source or emitter 88 at its edges secures the assemblage to the cabinet wall 18 as by screws. Thus the corrugated panel ridges 95 underlie the valleys or bases 92 of the infrared source 88; between the corrugated panel ridges 95 and the infrared source valleys or bases 92 are located corresponding ones of the opposing radiation bars 79 of heaters 72 and 74 for that source. Heater bars 79 directly heat corresponding infrared source or emitter valleys or bases 92 for effective heat transfer.

It will be appreciated that the infrared source or emitter 88 incorporates a shield to protect the sauna user from the high temperatures, on the order of 200 degrees or more Fahrenheit, of its valleys or bases 92; its closely spaced fins 90 even blocking finger user contact with the heated bases 92, and themselves having on free ends only maximum temperatures of 140 degrees.

While the infrared source or emitter 88 acts as a shield to protect the sauna user from the high temperatures of its valleys or bases 92, it also acts as a shield to protect the sauna user from the still higher temperatures of the electric infrared heaters 72 and 74.

It should be understood that not all of the radiation of the electric infrared heaters 72 and 74 is absorbed by the infrared source or emitter 88; some of the heater radiation passes through the valleys or bases 92 to directly heat the sauna user too.

Maintenance of the sauna is effected by simply wiping the finned infrared source 88 with a light cloth.

Actually, passage of the radiation from the heaters 72 and 74 to the sauna user may be facilitated by providing openings in the emitter valleys or bases 92 to allow its direct passage to the user rather than being intercepted by the valleys or bases. Then the infrared source or emitter 88 functions less as a radiation emitter and more as a shield.

Alternatively, the infrared source or emitter 88 may be almost totally converted to the shield function by mounting the fins 90 on a lattice work which minimally interrupts the flow of infrared radiation from the heaters 72 and 74 while allowing retention of the shield function of the fins.

While the emitter and/or shield 88 has been shown as embodying fins 90, it will be understood that other protrusions such as columns, pyramids or conical sections may extend upwards from the valleys or bases 92 or lattices; their spacing from each other being such as to prevent user contact with the hot bases or infrared heaters there behind, and to present comfortable-to-the-touch ends when the sauna is in use.

A strong physical cover 96 may be employed to protect the infrared source or emitter 58 on the cabinet back or rear wall 18 from the weight of a user leaning there against. The cover 96 may also be shaped to constitute a suitable and comfortable seat back for the user.

Figure 6:
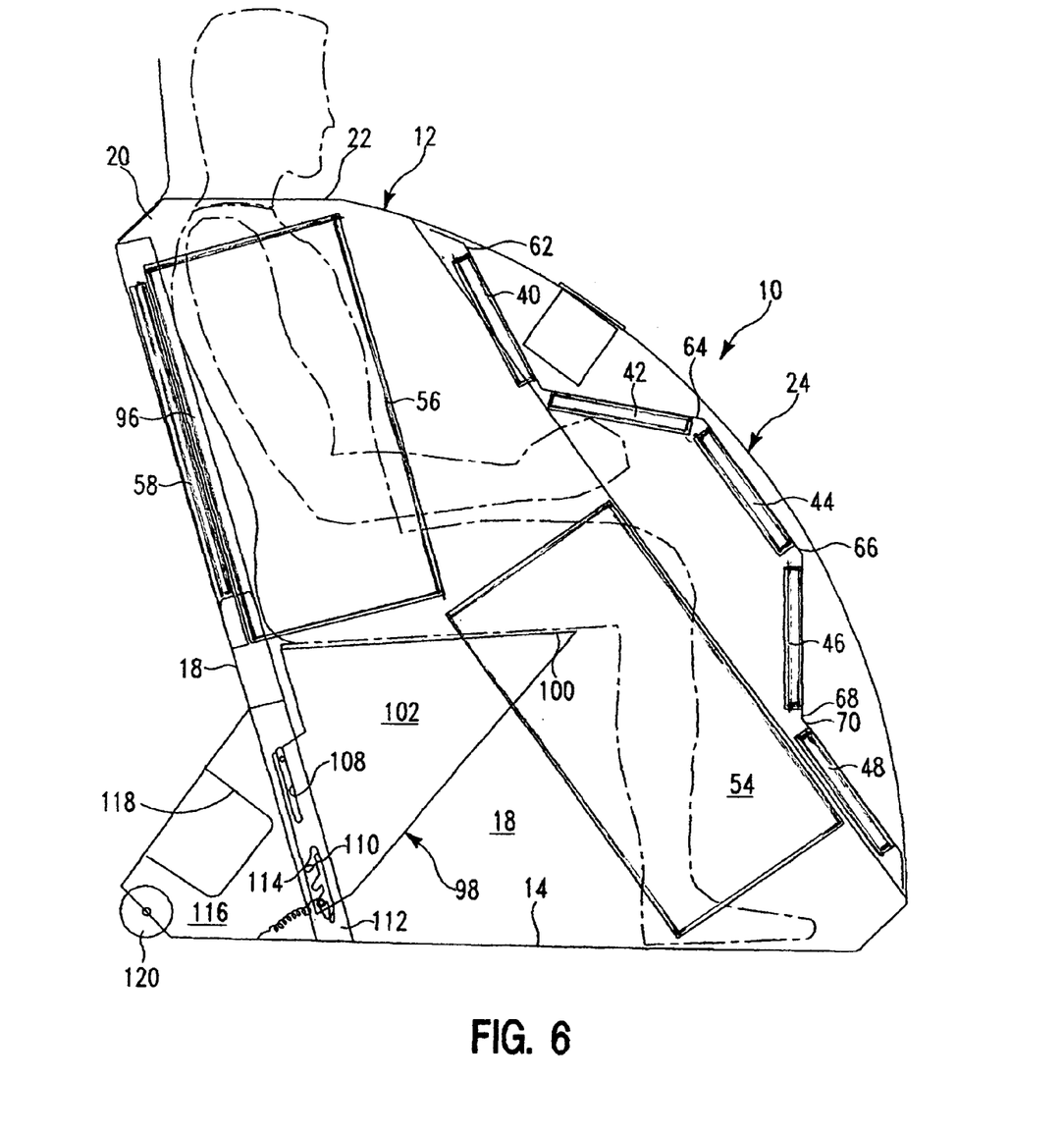
FIG. 6 is a diagrammatic view from the right side of the interior of a slightly modified version of the sauna shown in FIG. 1, with its door closed and showing a user seated on another type of adjustable seat.
Figure 9:
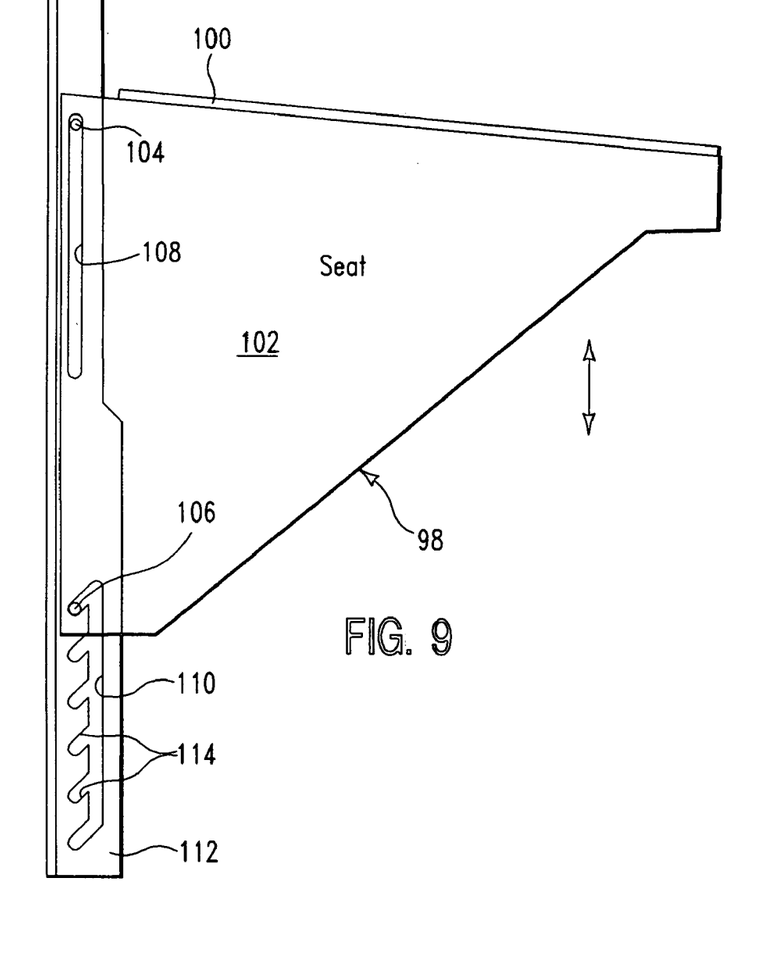
FIG. 9 shows in enlarged detail the adjustable seat in FIG. 6.

The sauna adjustable seat structure generally indicated by the numeral 98 in FIGS. 6 and 9 is supported more on the back wall 18 of the sauna, than that of FIG. 1 with the adjustable floor post 28. The seat structure 98 includes a top flat rectangular panel 100 and two supporting triangular side panels 102. The rear generally vertical edges of the panels 102 fixedly mount upper and lower headed pins 104 and 106 which are slidably received in upper and lower slots 108 and 110 formed in L-shaped brackets 112 suitably fixed to the cabinet rear wall 18. Rearwardly and downwardly extending side slots 114 off the lower slots 110 enable adjustment of the seat panel 100 to different heights to suit the build of the user.

Side panels 116 extending from the lower back of the cabinet and interconnected by brace 118, may be employed to mount a roller 120 to render the sauna very portable. The side panels 116 may also form part of a box to hold additional equipment for the sauna.

Figure 10:
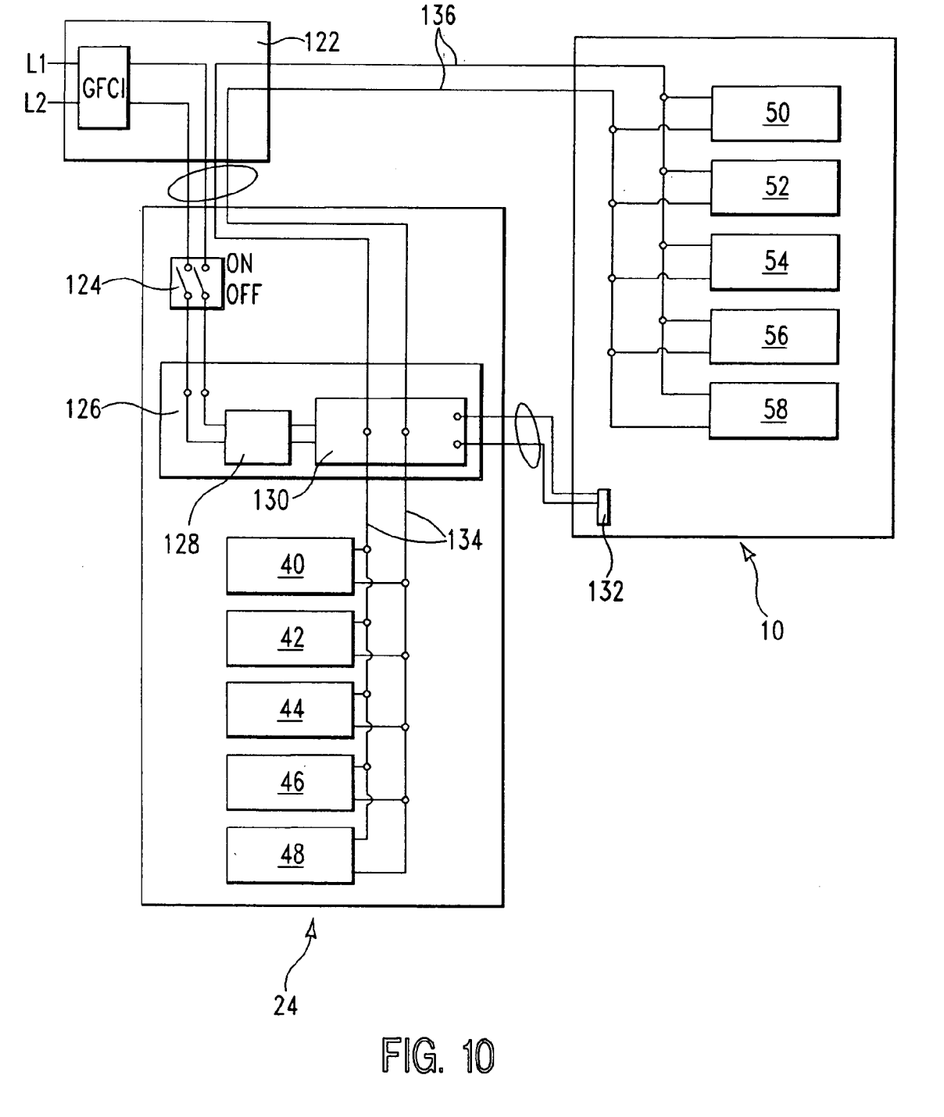
FIG. 10 is a schematic diagram of the circuits employed in the sauna.

The electrical connections for the sauna are shown schematically in FIG. 10. The electronics box 122 would be located under the seat to be out of the way of the user. An outlet cord, represented by power lines L1 and L2, would extend out of the box 122 and out of the sauna cabinet 10 for connection to any suitable source of AC 110 current, usually a home wall outlet. The lines L1 and L2 would be extended from the box 122 to a double pole On/Off switch 124 mounted on the cabinet door 24. From there, they would extend to a Temperature/Time Controller 126 through a Timier Circuit 128 to a Temperature Control Circuit 130 receiving controlling input through suitable wiring from a temperature sensor 132 mounted on a wall of the cabinet. Assuming that time guide provided by the timer circuit 128 is not exceeded and the temperature sensed by the sensor 132 is in the permissible range, the control circuit 130 will pass current to the door heaters 40–48 through power wires 134, and to the cabinet heaters 50–58 through power wires 136. The wires 134 and 136 will be connected to the individual ones of the dual heaters as shown in FIG. 2: the corresponding connectors at each end of the dual heaters being oppositely connected to the power lines L1 and L2. Thus as shown in FIG. 2, connector 78 of the top heater 72 will be connected to line L1 of lines 134 and connector 84 of the bottom heater 74 will be connected to line L2 of lines 134; whereas connector 80 of the top heater 72 will be connected to line L1 of lines 134 and connector 86 of the bottom heater 74 will be connected to line L1 of lines 134. Thus current will be flowing in opposite directions at any point in time in every pair of corresponding bars in the two heaters, to cancel essentially all AC current-induced ELF EMEs.

Figure 11:
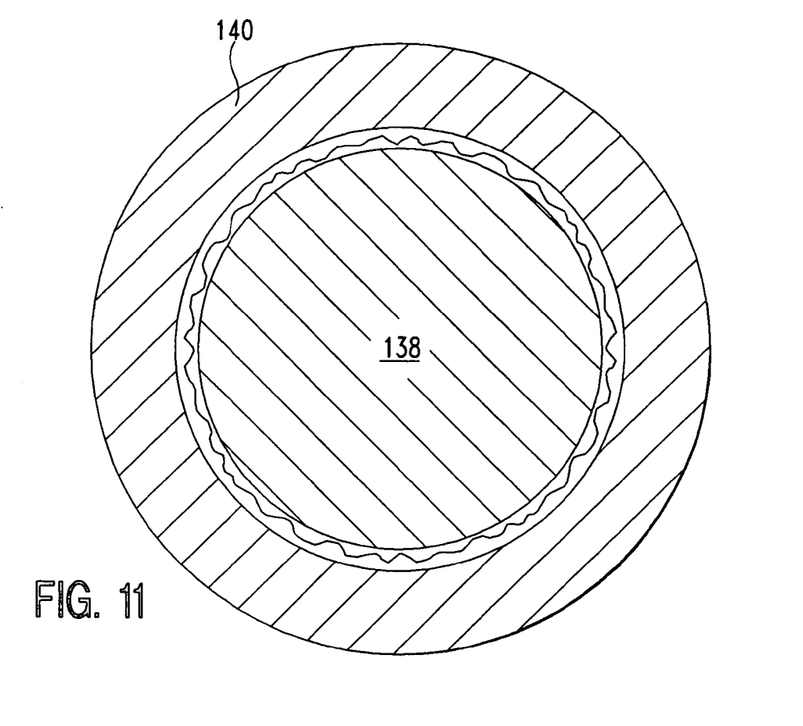
FIG. 11 is a cross-sectional view of low EMF power wiring constituted of a solid wire within a tubular wire.
Figure 12:
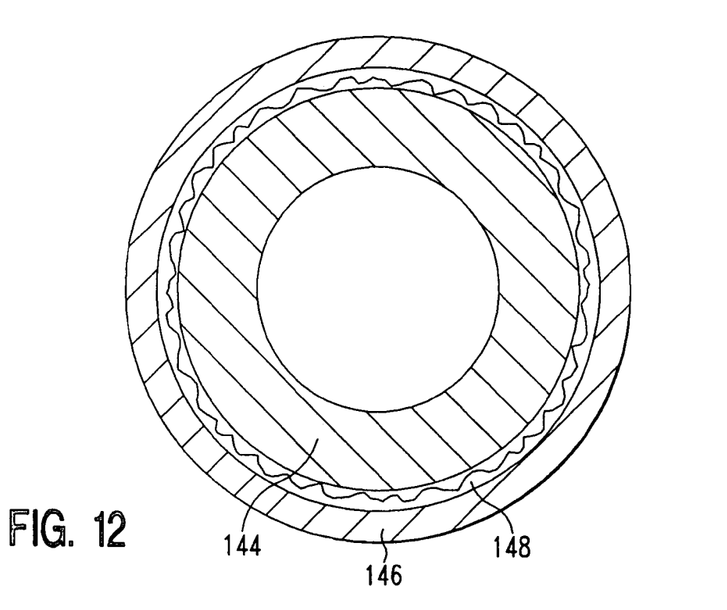
FIG. 12 is a cross-sectional view of even lower EMF power wiring constituted of a hollow wire within a tubular wire.
Figure 13:
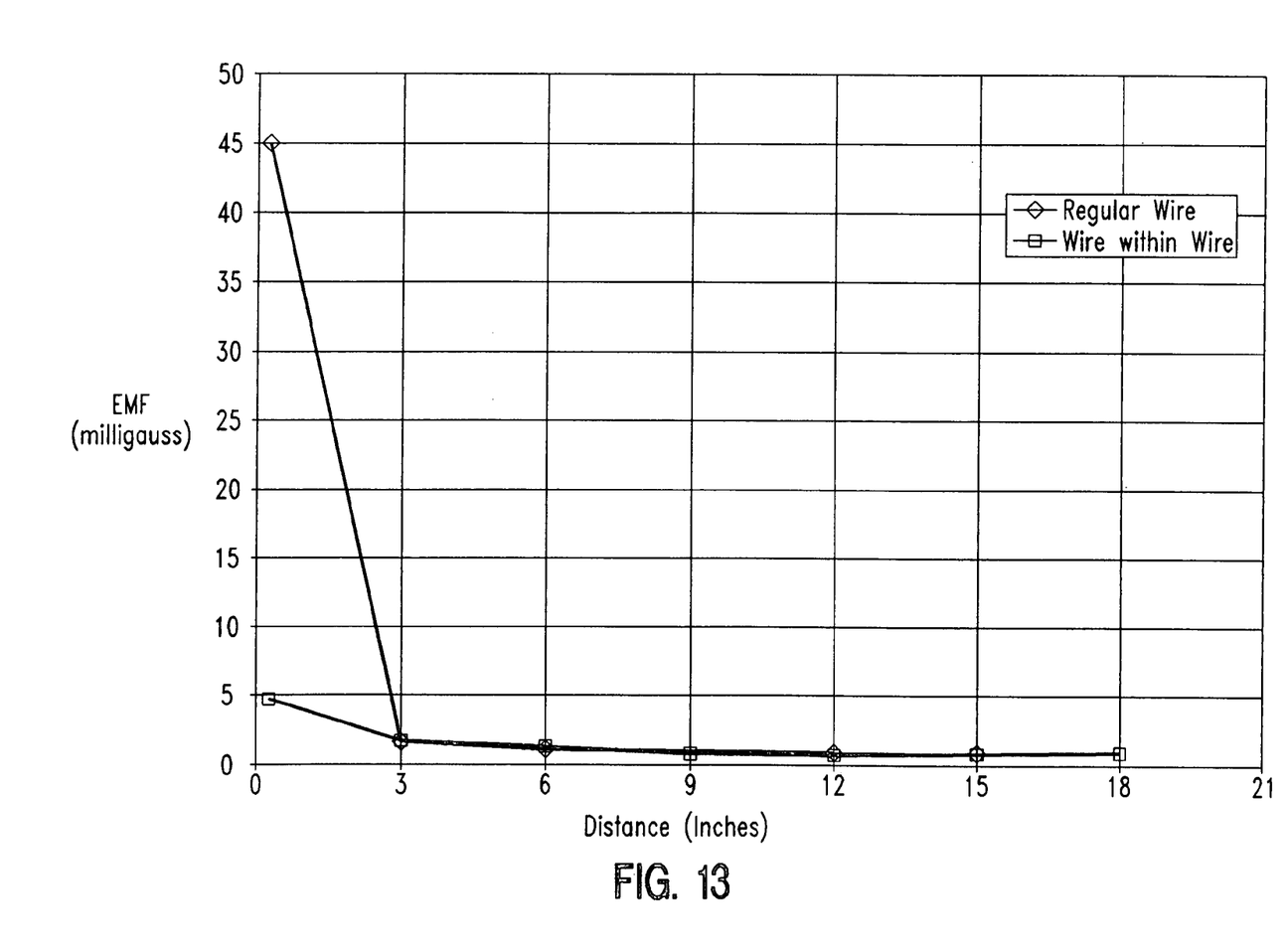
FIG. 13 is a chart depicting empirical evidence showing the high EMF resulting from regular (side by side) wire for power wiring, versus the low EMF resulting from using wire-within-wire power wiring.

In order to reduce if not eliminate ELF EMF due to the heater power lines such as 134 and 136, a round solid wire 138 may be mounted inside a tubular solid wire 140 but separated therefrom by an insulating material 142, as shown in FIG. 11. In FIG. 12, hollow wire 144 is mounted inside a thinner-walled tubular wire 146 to place the centers of current conductance closer to each other and hence more effective in EMF cancellation. Equal masses obtain in each of the wires of FIG. 11, and in each of the wires of FIG. 12, to accommodate equal current flow. The wires are separated from each other by an insulating material 148. FIG. 13 shows the significant reduction of measured EMF strength that obtains from the use of a wire within a wire instead of regular side-by-side power wiring. For a regular power wire, a high extremely-low-frequency EMF of 25 milligauss may obtain within one inch of it, and of about 16 milligauss at 3 inches. For the power wing of this invention, approximately only 1 milligauss obtains at even a nearness of 1 inch distance.

Figure 14:
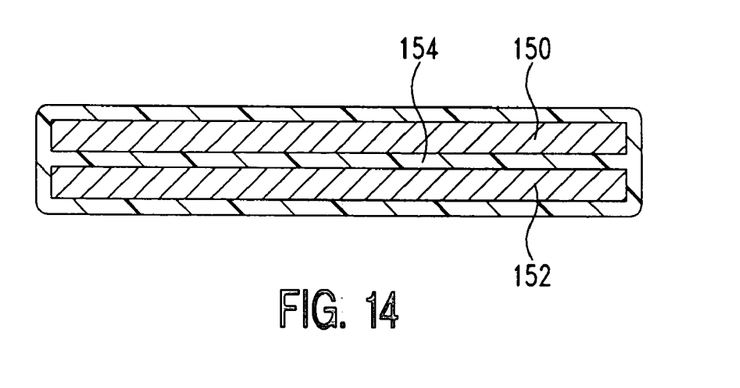
FIG. 14 is cross-sectional view of still lowerer EMF power wiring constituted of juxtaposed solid flat wires.

FIG. 14 shows still lower ELF EMF power wiring constituted of two juxtaposed solid flat wires 150 and 152 separated by a suitable plastic insulator also used to encapsulate the wires for safety. Equal masses obtain in the case of the wires 150 and 152, too.

An advantage of the invention, particularly in commercial applications, is that the sauna can be easily kept clean. The cabinet 12 including its door 24, seat structures 26 or 98, and infrared sources or emitters 88, are all made of impervious plastic, facilitating cleaning especially compared to wood-constructed saunas. The plastics chosen have low outgassing (the emission of plastic molecules into the air accompanied by an odor).

It will be appreciated that the finned infrared emitter and the dual infrared heater, singly and in combined assembly, may also be safely used in other close-range personal heating situations; e.g. at or under office desks and work stations; in domestic and institutional shower stalls; and near cribs, in hospital incubator rooms, and near bassinets for washing babies, etc., upon reducing the distance between the fins 90 of the emitter 88.

It will also be appreciated that the low ELF EMF feature of the dual heater of the invention allows the dual heater to be advantageously also used in floor, ceiling, and wall radiant-room heating systems; in bed, water bed, sofa, and massage table heating systems; and in car seat, boat seat, stadium seat, and submarine and ship barrack personnel heating systems.

While there has been shown and described preferred embodiments of the invention, it will be apparent to those skilled in the art that other and different applications may be made of the principles of the invention. It is desired therefore to be limited only by the scope or spirit of the appended claims.

What is claimed is:

1. An infrared heater comprised of two sets of parallel electrically-resistive bars, the corresponding bars of the respective sets being juxtaposed, electric conductors interconnecting corresponding ends of the bars, and connectors for applying 180 degrees out of phase electrical current to the respective sets of conductors so that current flows in opposite directions in corresponding bars at any given point in time, and a protrusioned infrared source comprised of a base adapted to be heated to uncomfortable-to-the-touch temperatures, and protrusions which project away from the base and present temperatures comfortable to the touch when the base is at uncomfortable temperatures, wherein the protrusioned-infrared-source base is finned and has valleys between the fins, and the valleys overlie corresponding electrically-resistive bars, and a panel for spacing the heater from any wall on which it may be mounted, wherein the panel is corrugated and its ridges underlie corresponding resistive bars, wherein the fins are separated by less than finger width, and a cabinet having a door mounting the heater on the inside.

* * * * *